US00PP23542P2

(12) United States Plant Patent
Hatch

(10) Patent No.: US PP23,542 P2
(45) Date of Patent: Apr. 16, 2013

(54) ***AGAPANTHUS* PLANT NAMED 'PAVLOVA'**

(50) Latin Name: *Agapanthus hybrida*
Varietal Denomination: Pavlova

(76) Inventor: Lindsey Hatch, Auckland (NZ)

( * ) Notice: Subject to any disclaimer, the term of this patent is extended or adjusted under 35 U.S.C. 154(b) by 0 days.

(21) Appl. No.: 13/374,661

(22) Filed: Jan. 5, 2012

(51) Int. Cl.
*A01H 5/00* (2006.01)

(52) U.S. Cl. ..... Plt./398

(58) Field of Classification Search ..... Plt./398
See application file for complete search history.

*Primary Examiner* — June Hwu
*Assistant Examiner* — Louanne Krawczewicz Myers
(74) *Attorney, Agent, or Firm* — Mark P. Bourgeois

(57) ABSTRACT

A new cultivar of *Agapanthus* plant named 'Pavlova' that is characterized by grey green leaves, a compact dwarf habit and a large number of white flowers.

1 Drawing Sheet

Botanical classification: *Agapanthus hybrida.*
Variety denomination: 'Pavlova'.

BACKGROUND OF THE INVENTION

The present invention relates to a new and distinct cultivar of *Agapanthus* plant botanically known as *Agapanthus hybrida* and hereinafter referred to by the cultivar name 'Pavlova'.

'Pavlova' originated from the crossing of the female or seed parent plant an unnamed *Agapanthus inapertus* cultivar (not patented) and the male or pollen parent plant an unnamed *Agapanthus praecox* cultivar (not patented) . 'Pavlova' was selected as a single plant within the progeny of the stated cross in a controlled environment in Pukekohe, Auckland, New Zealand in 2002.

Asexual reproduction of the new cultivar 'Pavlova' first occurred by tissue culture in 2002 in Avondale, Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Agapanthus* cultivar 'Pavlova'. These traits in combination distinguish 'Pavlova' as a new and distinct cultivar apart from other existing known varieties of *Agapanthus.*

1. *Agapanthus* 'Pavlova' exhibits grey green leaves.
2. *Agapanthus* 'Pavlova' exhibits a compact dwarf habit.
3. *Agapanthus* 'Pavlova' exhibits a large number of white flowers.

The closest comparison cultivars are *Agapanthus* 'Finn' (not patented) and *Agapanthus* 'Silver Baby' (not patented).

'Pavlova' is distinguishable from 'Finn' by the following characteristics:

1. 'Pavlova' exhibits grey green leaves. The leaves of 'Finn' are green.
2. 'Pavlova' exhibits a shorter overall height than 'Finn'.

'Pavlova' is distinguishable from 'Silver Baby' by the following characteristics:

1. 'Pavlova' exhibits grey green leaves. The leaves of 'Silver Baby' are green.
2. 'Pavlova' exhibits a larger overall height than 'Silver Baby'.
3. 'Pavlova' exhibits white flowers. The flowers of 'Silver Baby' are silver white with a blue tinge.

'Pavlova' is distinguishable from the unnamed female or seed parent *Agapanthus inapertus* cultivar by the following characteristics:

1. 'Pavlova' exhibits lighter green leaves.
2. 'Pavlova' exhibits a larger overall height.
3. 'Pavlova' exhibits lighter colored white flowers.

'Pavlova' is distinguishable from the unnamed male or pollen parent *Agapanthus praecox* cultivar by the following characteristics:

1. 'Pavlova' exhibits darker green leaves.
2. 'Pavlova' exhibits a more compact habit and a shorter overall height.

BRIEF DESCRIPTION OF THE DRAWING

The accompanying photograph illustrates the distinguishing traits of *Agapanthus* 'Pavlova'. The plants in the photograph show an overall view of 1 year old plants grown outdoors in Pukekohe, Auckland, New Zealand. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Agapanthus* cultivar named 'Pavlova'. Data was collected in Pukekohe, Auckland, New Zealand from 1 year old outdoor grown plants. The time of year was Summer in the Southern Hemisphere and the temperature range was 19-24 degrees Centigrade during the day and 15-18 degrees Centigrade at night. The light level was natural outdoor light. Color determinations are in accordance with The Royal Horticultural Society Colour Chart 2001 edition, except where general color terms of ordinary dictionary significance are used. The growing requirements are similar to the species. 'Pavlova' has not been tested under all possible conditions and phenotypic differences may be observed with variations in environmental, climatic, and cultural conditions, however, without any variance in genotype.

Botanical classification: *Agapanthus hybrida* 'Pavlova'.

Use: Ornamental Perennial.

Parentage: 'Pavlova' originated from the crossing of the female or seed parent plant an unnamed *Agapanthus inapertus* cultivar and the male or pollen parent plant an unnamed *Agapanthus praecox* cultivar.

Vigor: High.

Growth habit: Upright.

Plant shape: Basal leaves with central flowering scapes.

Overall height: 45 cm. in height.

Overall width: 45 cm. in width.

Low temperature tolerance: −5° Centigrade.

High temperature tolerance: 40° Centigrade.

Propagation: Tissue culture.

Crop time: 6 months to produce a finished liner plant.

Root system: Thick, fleshy, white-grey in color.

Foliage:

*Leaf arrangement*.—Basal.
*Compound or single*.—Single.
*Quantity of leaves per plant*.—About 20.
*Texture*.—Smooth.
*Leaf shape*.—Linear.
*Leaf apex*.—Acute.
*Leaf base*.—Cuneate.
*Leaf length*.—24 cm. in length.
*Leaf width*.—2 cm. in width.
*Pubescence*.—Absent.
*Leaf margin*.—Entire.
*Young leaf color* (*lower surface*).—137C.
*Young leaf color* (*upper surface*).—137C.
*Mature leaf color* (*lower surface*).—137C.
*Mature leaf color* (*upper surface*).—137C.
*Vein color* (*under surface*).—137C.
*Vein color* (*upper surface*).—137C.
*Venation pattern*.—Parallel.
*Leaf attachment*.—Sessile.

Flower:

*Inflorescence arrangement*.—Campanulate flowers arranged in umbels on erect scapes.
*Natural flowering season*.—Summer.
*Fragrance*.—None.
*Inflorescence size*.—8 cm. in length and 12 cm. in width.
*Quantity of flowers per inflorescence*.—Approximately 55.
*Flower bud length*.—25 mm. in length.
*Flower bud diameter*.—8 mm. in diameter.
*Flower bud shape*.—Oblong.
*Bud color*.—N155A.
*Flower aspect*.—Upright.
*Flower shape*.—Campanulate.
*Flower dimensions*.—12 mm. in diameter and 30 mm. in height.
*Flower longevity*.—Approximately 4 weeks.
*Tepal texture*.—Smooth.
*Number of tepals*.—8.
*Fused or unfused*.—Lower 50% are fused.
*Tepal shape*.—Oblanceolate to ovate.
*Tepal margin*.—Repand.
*Tepal apex*.—Rounded.
*Tepal base*.—Rounded.
*Tepal length*.—30 mm. in length.
*Tepal width*.—6 mm. in width.
*Tepal color when opening* (*upper side*).—N155A.
*Tepal color when opening* (*under side*).—N155A.
*Tepal color fully opened* (*upper side*).—N155A.
*Tepal color fully opened* (*under side*).—N155A.
*Self-cleaning or persistent*.—Persistent.

Peduncle:

*Peduncle dimensions*.—45 cm. in length and 2 cm. in diameter.
*Peduncle angle*.—0 to 15° from vertical.
*Peduncle color*.—137C.
*Peduncle strength*.—Strong.

Pedicels:

*Pedicel dimensions*.—20 mm. in length and 1.5 mm. in diameter.
*Pedicel color*.—137C.
*Pedicel strength*.—Moderate.

Reproduction organs:

*Stamen number*.—Average 6.
*Anther shape*.—Oval.
*Anther size*.—Average 2 mm.
*Anther color*.—97D.
*Amount of pollen*.—Low.
*Pistil number*.—Average 1.
*Pistil length*.—Average 30 mm. in length.
*Stigma shape*.—Trifid.
*Stigma color*.—91D.
*Ovary color*.—133B.

Fruit/seed production: Plants of the new cultivar are sterile.

Disease and pest resistance: Plants of the new cultivar have not been observed for disease and pest resistance.

The invention claimed is:

1. A new and distinct variety of *Agapanthus* plant named 'Pavlova' as described and illustrated.

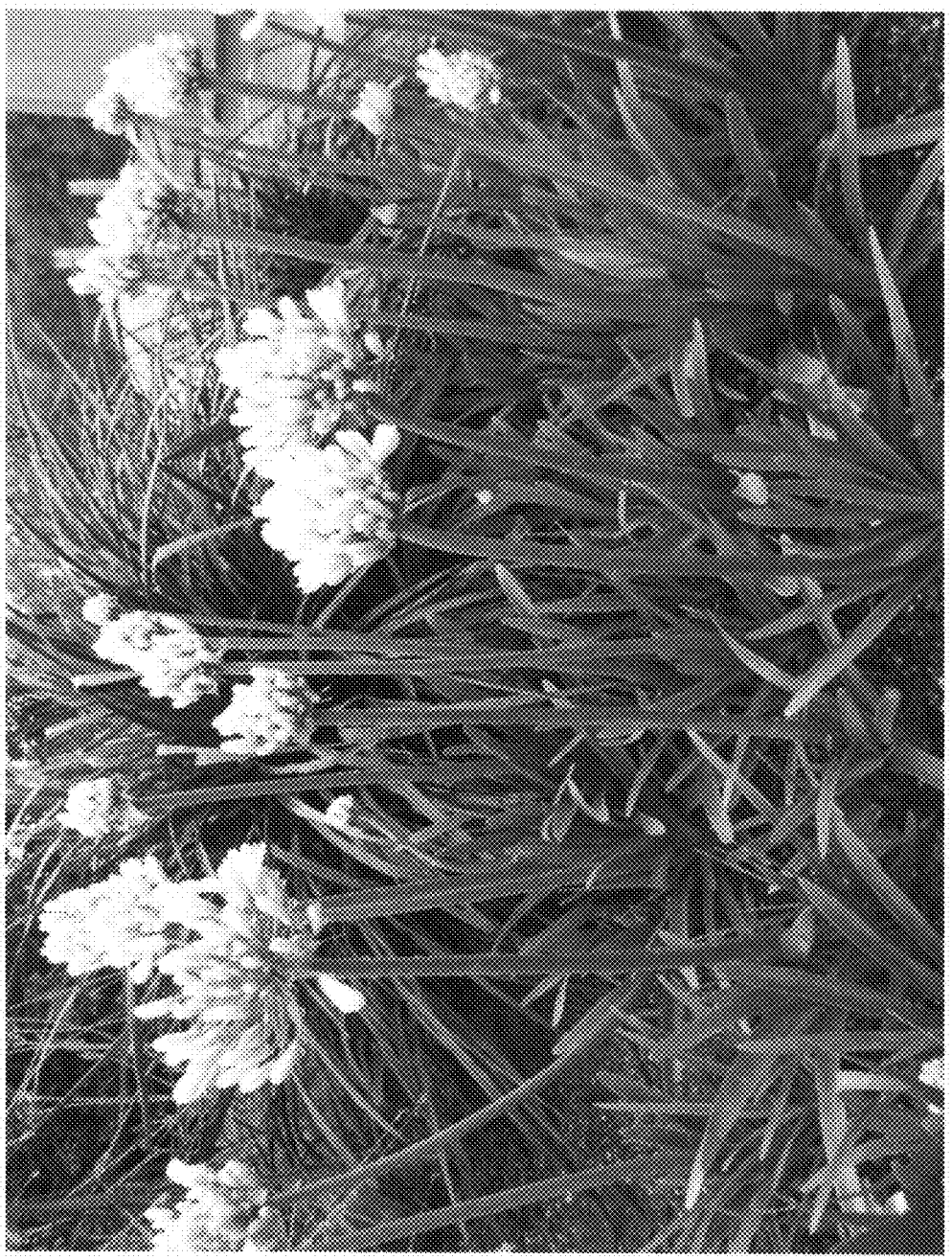

* * * * *